US006465701B1

(12) United States Patent
Marsella et al.

(10) Patent No.: US 6,465,701 B1
(45) Date of Patent: Oct. 15, 2002

(54) CATALYST AND OXYCHLORINATION PROCESS USING IT

(75) Inventors: Andrea Marsella, Paese; Pierluigi Fatutto, Mestre; Diego Carmello, Mogliano Veneto, all of (IT)

(73) Assignee: EVC Technology AG (CH)

( * ) Notice: Subject to any disclaimer, the term of this patent is extended or adjusted under 35 U.S.C. 154(b) by 0 days.

(21) Appl. No.: 09/567,282

(22) Filed: May 8, 2000

(30) Foreign Application Priority Data

May 21, 1999 (EP) ............................................. 99303973

(51) Int. Cl.⁷ ............................................... C07C 17/15
(52) U.S. Cl. ...................................................... 570/245
(58) Field of Search ......................................... 570/245

(56) References Cited

U.S. PATENT DOCUMENTS

| | | |
|---|---|---|
| 2,408,164 A | 9/1946 | Foster |
| 3,966,644 A | 6/1976 | Gustafson |
| 4,283,307 A | 8/1981 | Barone et al. |
| 4,366,093 A | 12/1982 | Shiozaki et al. |
| 4,382,021 A | 5/1983 | Laurer et al. |
| 4,438,217 A | 3/1984 | Takata et al. |
| 4,740,644 A | 4/1988 | Eichhorn et al. |
| 5,034,369 A | 7/1991 | Hebrard et al. |
| 5,082,819 A | 1/1992 | Boeck et al. |
| 5,166,120 A | 11/1992 | Deller et al. |
| 5,905,054 A | * 5/1999 | Cavalli et al. ............... 570/245 |

FOREIGN PATENT DOCUMENTS

| | | |
|---|---|---|
| EP | 0 054 674 | 6/1982 |
| EP | 0 102 641 | 3/1984 |
| EP | 0 464 633 A1 | 1/1992 |
| WO | WO 96/40431 | 12/1996 |

* cited by examiner

*Primary Examiner*—Alan Siegel
(74) *Attorney, Agent, or Firm*—Woodcock Washburn LLP

(57) ABSTRACT

The present invention provides a cylindrical hollow moulded catalyst having an outer diameter ranging from about 4 mm to about 7 mm, an inner diameter ranging from about 2 mm to about 2.8 mm, length ranging from about 6.1 mm to about 6.9 mm, and the ratio of the outer diameter to the inner diameter ranging from about 2 to about 2.5. The molded catalyst of the present invention is effective in the oxychlorination process, has a low resistance to flow, allows for good heat exchange with the wall of an industrial reactor and, with a suitable active phase based on copper and such additives as alkali metals, alkaline earth metals, group IIIB metals and lanthanides, is a good catalyst for fixed bed oxychlorination processes.

44 Claims, 1 Drawing Sheet

CATALYST AND OXYCHLORINATION PROCESS USING IT

REFERENCE TO RELATED APPLICATIONS

Figure 1:
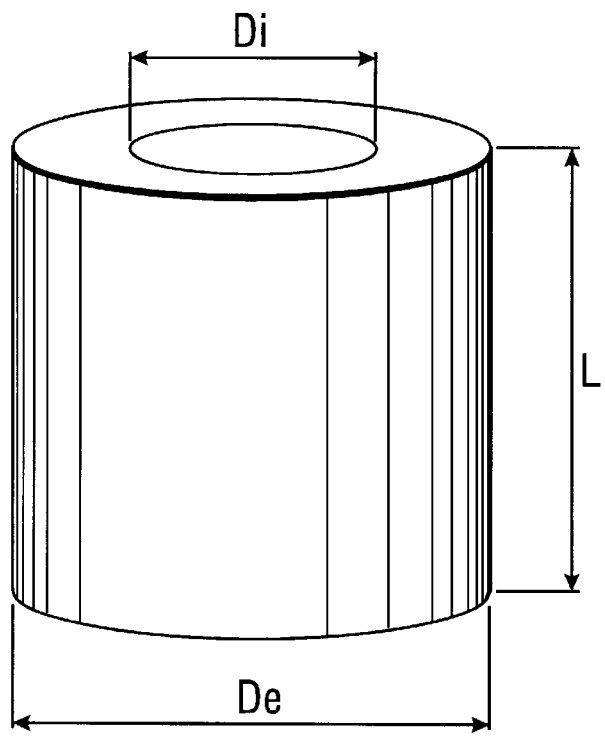

This application claims priority under 35 U.S.C. § 119(a) to European Application Ser. No. 99303973.4, filed May 21, 1999, incorporated herein by reference in its entirety.

Field of the Invention

This invention relates to a novel catalyst, suitable for oxychlorination of hydrocarbons. It is especially concerned with a catalyst for the oxychlorination of ethylene to 1,2-dichloroethane (EDC).

The vapour-phase oxychlorination of ethylene to EDC using a fixed bed reactor containing a supported catalyst, usually a supported copper catalyst, is widely used commercially, for example as part of the process for producing vinyl chloride monomer (VCM). The industry is constantly seeking to improve the efficiency of the process, and much work has been reported on the effects which different catalysts have on the process. Thus both the composition and physical presentation of the catalyst has been studied. The present invention is concerned in particular with the physical shape of the catalyst.

Over the last few years improvements have been reported in catalytic performance obtained by suitable modification of the shape and/or size of catalysts in pellet form. Such characteristics affect some of the most important properties of the catalytic bed in fixed bed reactors, such as i) the resistance of the reactant flux (pressure drop), which determines the maximum possible flow through the reactor; ii) the efficiency of heat exchange, which allows the removal of heat from the highly exothermic oxychlorination reaction; and iii) the effectiveness of the pellet as far as the diffusion of reactants and reaction products inside the pellets is concerned.

A low pressure drop allows the flow through the catalytic bed, and therefore the productivity of industrial reactors, to be increased. On the other hand because a reason for replacing the catalysts in industrial reactors is the increase of the pressure drop with the catalyst life, an initial low pressure drop allows a larger range of pressure drop and consequently a longer use of the catalysts before they need replacing. Starting from the usual catalysts, shaped as spheres or solid cylinders, a lower pressure drop through the catalytic bed has been obtained by developing catalysts based on columnar configurations, through hollowed pellets shaped with circular or multilobed cross-sections, which give rise to catalytic beds with higher void fractions.

Catalysts of this type, for use in oxychlorination reactions, have been described for example in the following patent specifications. U.S. Pat. No. 4,366,093 describes a hollowed cylindrical catalyst having an outer diameter $D_e$ in the range 3–6 mm, an internal diameter $D_i \geq 1$ mm, a wall thickness of at most 1.5 mm and a length L in the range 3–6 mm.

U.S. Pat. No. 4,382,021 and EP-A-054674 report a hollowed cylinder catalyst having the dimensions $D_e$=5–12 mm, $D_i$=3–8 mm and L=3–12 mm.

U.S. Pat. No. 4,740,644 claims a new method for preparing hollowed cylinder catalysts, and exemplifies catalysts with $D_e$=5 mm, $D_i$=1.8 mm and L=5 mm.

In U.S. Pat. No. 5,166,120 a catalyst prepared via extrusion, shaped as a hollowed cylinder with $D_e$=4–6 mm, $D_i$=1–2 mm and L=1.7–3.75 $D_e$ is described.

WO 96/40431 describes a catalyst for ethylene oxychlorination which is shaped as a hollowed cylinder with internal reinforcing vanes, with $D_e \geq 6.5$ mm, wall thickness in the range of 0.1–0.3. $D_e$ and L=0.5–5. $D_e$.

Hollow cylindrical pellets have a S/V (geometric surface to volume ratio) higher than spheres and solid cylinders, and this, together with a higher catalytic bed voidage, gives a more efficient heat exchange. Thus, better temperature control along the catalytic bed and reduced hot spot temperatures are obtained: in this way a longer catalyst life is achieved and the reaction results in a reduced formation of chlorinated by-products and combustion products.

A further benefit of hollowed cylindrical pellets, due to the higher geometric surface combined with a lower wall thickness of the pellets, is the higher effectiveness of the pellets, because the reaction takes place only in a thin external layer. Moreover, the formation of carbonaceous deposits inside the core of the pellet wall, which causes pellet breakage and pressure drop increase during industrial run, is reduced. Consequently, a further increase of productivity and catalyst life can be obtained.

In spite of the above described advantages a hollowed pellet must be designed carefully, since otherwise several disadvantages become evident. For example, if the $D_i/D_e$ ratio of a hollowed cylinder is greater than a certain value, the pellet becomes too fragile, without further advantage in terms of effectiveness. Moreover the apparent bulk density of the catalyst decreases, resulting in a lower conversion per unit volume of catalyst bed due to the lower total active phase content. This last effect can affect also the catalyst life, because the catalyst tends to lose active phase compounds in the reaction environment. A solution to this problem is to increase the active phase concentration of fresh catalyst, also because an excess of active phase compounds, even if not contributing directly to the catalyst activity, can act as a reservoir for the pellet, increasing the catalyst life. However the Cu concentration can not be increased over a certain extent, because the consequent loss of the catalyst surface area causes a loss of activity.

The above described problems can also be encountered if a more favourable pressure drop of catalyst shaped as hollowed cylinders is pursued by increasing $D_e$ or L with a constant $D_i/D_e$ ratio. A further disadvantage of this approach is that a too high increase of $D_e$ or L can cause an inhomogeneous loading of the catalyst inside the reactor.

The above remarks make it clear that, in terms of oxy catalysts in pellet shape it must be taken into account that every change capable of giving rise to some improvement in catalytic performance can also cause unwanted detrimental effects, especially if the changes are not balanced carefully by the simultaneous modification of other characteristics. As a conclusion, in order to obtain an excellent oxy catalyst it is not sufficient to optimise a single characteristic; all the properties as a whole, responsible for different effects, must be carefully balanced.

The present invention has for its primary object to provide a catalyst for effective use in oxychlorination reactions. A further object of the invention is to provide a catalyst which satisfies the above described requirements of lower pressure drop of the catalytic bed, better heat exchange and good effectiveness without the disadvantages reported above.

According to the invention there is provided a catalyst comprising a carrier and catalytically-active material comprising copper supported thereon, the copper being present in an amount of 1–12 wt % on the dry catalyst, wherein the catalyst is in the form of a hollow cylinder having the following dimensions:

$$4.0 \leq D_e \leq 7.0 \tag{1}$$

$$2.0 \leq D_i \leq 2.8 \tag{2}$$

$$6.1 \leq L \leq 6.9 \tag{3}$$

-continued $$2.0 \leq D_e/D_i \leq 2.5 \quad (4)$$

wherein $D_e$ is the external diameter (mm), $D_i$ is the internal diameter (mm) and L is the length (mm), respectively, of the hollow cylinder.

The invention also provides the use of such a catalyst in the oxychlorination of hydrocarbons, especially the vapour phase oxychlorination of ethylene to EDC.

In the preferred form of the catalyst of this invention, the hollow cylindrical pellets have dimensions $D_e$=4.5 to 5.5 mms, $D_i$=2.0 to 2.6 mms, and L=6.2 to 6.6 mms and $D_e/D_i$ is in the range 2.1 to 2.3. The catalysts of the invention are especially effective when used in tubular reactors having diameters in the range 25 to 50 mms.

The carrier material of the catalyst of the invention may be any of the materials known for producing copper-supported catalysts. Examples include silica, pumice, diatomaceous earth, alumina, and other aluminium hydroxo compounds such as boehmite and bayerite. The preferred carrier materials are γ-alumina and boehmite, the latter normally being pre-heat treated to convert it into alumina. The carrier material suitably has a surface area (BET) of 50–350 $m^2/g$.

The catalytically-active material supported on the carrier contains copper in an amount of 1–12 wt %, based on the weight of the dry catalyst. The copper will normally be deposited on the carrier in the form of a salt, especially a halide, and preferably as cupric chloride.

The copper may be used in combination with other metal ions, in order to assist in the attainment of the desired selectivity and conversion performance. Such other metals include, for example, alkali metals (such as Li, Na, K, Ru, Cs), alkaline-earth metals (such as Mg, Ca, Ba), group IIB metals (such as Zn and Cd) and lanthanides (such as La, Ce and so on) or a suitable combination of them. These additional metal ions can be added as salts or oxides, the total amount of additives suitably being in the range 0–10 wt %. They can be added together with the copper or alternatively one or more of them (even all) after or even before the copper. In the last case their addition can be followed by an intermediate heat treatment. Preferred alkali metals are Li and K and they are preferably added as chlorides, each of them in the range 0–6 wt %. The preferred alkaline-earth metal is Mg, added in the range 0–6 wt %. Preferred lanthanides are La and Ce, each of them added in the range 0–6 wt %.

The addition of the catalytically-active components can be accomplished by methods well known by those of skill in catalyst preparation. There may be mentioned, for example, dry impregnation, incipient wetness impregnation or dipping, using a suitable solution of compounds to be added, for example an aqueous solution, optionally containing also acids such as HCl.

The addition of the active components can be made partially or totally before or after the formation of the hollow pellets. Preferably the catalysts are prepared by impregnation of the already formed carrier.

The shaping of the carrier or the catalyst may be performed by well known methods such as tabletting and extrusion. These operations are performed in the usual manner, optionally using additives such as lubricants and/or binders. Preferably the shaped pellets are obtained by tabletting, to attain a more uniform pellet size, density and higher mechanical resistance. The operations include customary thermal treatments, such as calcination of the carrier at 500–1100° K, preferably at 750–950° K, if the active part is added to the carrier after the shaping procedure and drying at 330–500° K after addition of the active components.

Figure 2:
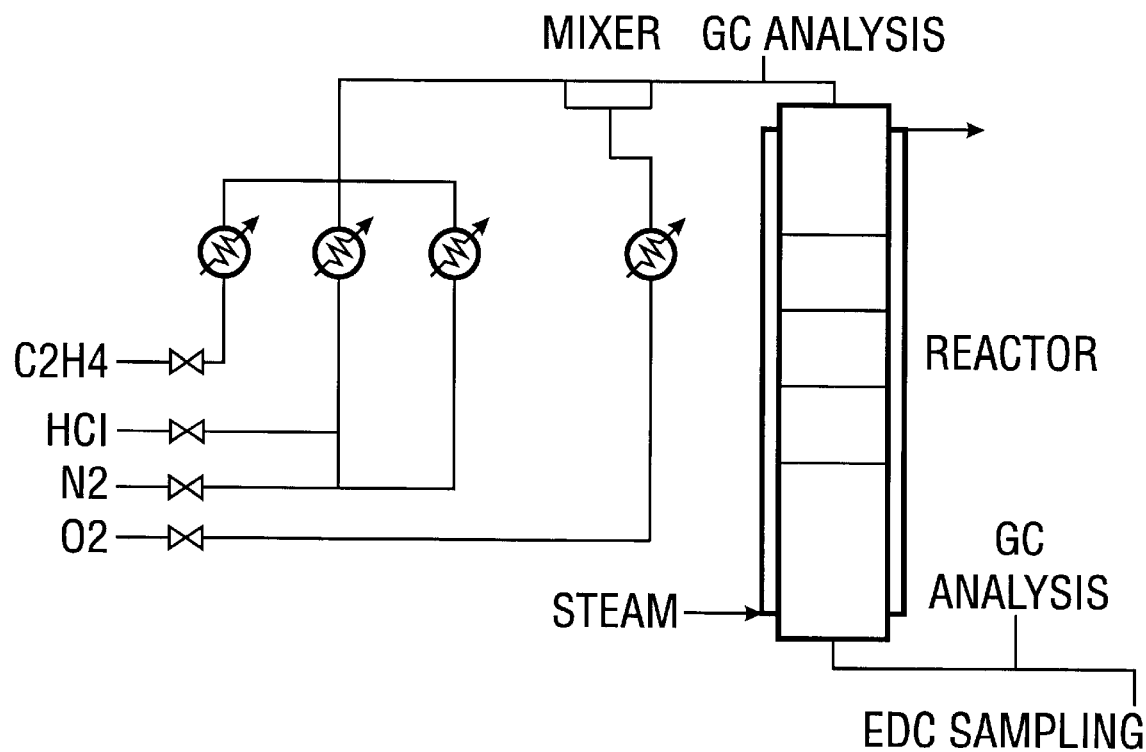

In the accompanying drawings,

FIG. 1 is a schematic illustration, not to scale, of a catalyst pellet according to the invention; and FIG. 2 is a flow diagram illustrating the catalytic oxychlorination of ethylene to 1,2-dichloroethane (EDC).

With reference to FIG. 1, the catalyst pellets of the invention are in the form of a hollow cylinder of a carrier material supporting a copper-containing active material, the pellet having the dimensions $D_e$=4.0 to 7.0 mms, $D_i$=2.0 to 2.8 mms and L=6.1 to 6.9 mms and $D_e/D_i$ is in the range 2.0 to 2.5. In the preferred aspect of the invention the pellets are made by extruding or tabletting a mixture of carrier material, and lubricants and/or binders as appropriate, and then impregnating the fixed carrier with the copper-containing catalytically-active component.

The pellets of catalyst are charged into the reactor shown in FIG. 2, which shows in schematic form a plant for the catalytic oxychlorination of ethylene. A mixture of ethylene, hydrogen chloride and nitrogen is fed to a mixer, where it is mixed with oxygen and the resulting gaseous mix is admitted to the reactor. The reactor is surrounded by a steam-filled jacket to adjust its temperature.

The following Examples and Comparative Examples are given to illustrate, but not to limit, the invention.

EXPERIMENTAL EQUIPMENT AND EXAMPLES

The choice of the method used for catalytic activity testing is very important, because the differences in term of conversion and selectivity to different products exhibited by different catalysts are usually small, but of great importance in large scale dichloroethane production. The only way to obtain results which are truly representative of the industrial reactor is to perform the test using a tube with the same size as an industrial one and to adopt the same conditions (temperature, pressure, feed composition, flow and so on) as those used in the industrial reactor. The data reported below were obtained in a pilot plant using a tube having the same size as a typical industrial one and under a variety of different reaction conditions covering those encountered during a typical industrial run. See FIG. 2.

The reactor used was a nickel tube 8 m long, with an internal diameter of 27.75 mm. An external jacket with circulating steam was used to control the temperature profile. The reactor was equipped with a thermowell having an external diameter of 6 mm, containing 12 thermocouples to record the temperature profile during the tests. Two on-line gaschromatographs were used at the inlet and at the outlet of the reactor to control the reaction. The EDC was collected in a vessel containing isopropyl alcohol at about 0° C. and then analysed. This technique allows the collection also of the low boiling and the water soluble compounds (chloroethanol, chloral etc.) as well as the unreacted HCl. The reactor feed was: 5200 Nl/h of ethylene, 600 Nl/h of $O_2$, 2300 Nl/h of HCl, 1000 Nl/h of $N_2$. The oxygen was 6.5 vol % (the flammability limit at 210° C. and at 6 barg is ca. 8%). The pressure at the inlet of the reactor was 6 barg, and the temperature of the coolant was 220° C.

Four different types of catalysts in the form of hollow cylinder pellets having the shapes and sizes shown in Table 1 and the compositions shown in Table 2 were prepared on the basis of the method described above. In particular, aluminium stearate as a lubricant was added to boehmite and the mixture was moulded into a particle having the shape and size shown in Table 1, by using a tabletting machine. Catalyst A was formed according to the present invention, catalyst B according to U.S. Pat. No. 4,366,093, catalyst C according to U.S. Pat. No. 4,740,644 and catalyst D according to U.S. Pat. No. 5,166,120.

The carrier pellets were then calcined at 500–600° C. for 5 hours, to obtain pellets made of γ-$Al_2O_3$ with the required surface area. The carrier was impregnated by the incipient wetness method with solutions containing the appropriate concentration of active compounds in order to obtain the catalysts with the compositions set out in Table 2.

TABLE 1

| CATALYST | | A | B | C | D |
|---|---|---|---|---|---|
| De | (mm) | 4.90 | 4.90 | 5.00 | 4.90 |
| Di | (mm) | 2.25 | 2.25 | 1.80 | 1.30 |
| L | (mm) | 6.35 | 5.00 | 5.00 | 9.50 |
| Volume | (mm3) | 94.5 | 74.4 | 85.5 | 166.5 |
| Geometric surface area | (mm2) | 172.3 | 142.0 | 141.0 | 225.0 |
| V/S | (mm) | 0.548 | 0.524 | 0.606 | 0.740 |
| Bed void fraction* | | 0.570 | 0.554 | 0.532 | 0.640 |

*Bed Void Fraction = (Volume of catalyst bed − Volume of pellets)/Volume of catalyst bed = = 1 − (Bulk density/Pellet density)

TABLE 2

| CATALYST | | A1 | A2 | B1 | B2 | C1 | C2 | D1 | D2 |
|---|---|---|---|---|---|---|---|---|---|
| Carrier | | γ-Al2O3 | γ-Al2O3 | γ-Al2O3 | γ-Al2O3 | γ-Al2O3 | γ-Al2O3 | γ-Al2O3 | γ-Al2O3 |
| CuCl2 | (% wt.) | 9.5 | 17 | 9.5 | 17 | 9.5 | 17 | 9.5 | 17 |
| KCl | (% wt.) | 5.7 | 1.5 | 5.7 | 1.5 | 5.7 | 1.5 | 5.7 | 1.5 |
| Surface area | (m2/g) | 120 | 150 | 124 | 155 | 125 | 153 | 124 | 152 |
| Bulk density | (kg/l) | 0.69 | 0.71 | 0.73 | 0.75 | 0.76 | 0.78 | 0.55 | 0.58 |

TABLE 3

| CATALYST | | A | | | B | | | C | | | D | | |
|---|---|---|---|---|---|---|---|---|---|---|---|---|---|
| TRIAL | | 1 | 2 | 3 | 1 | 2 | 3 | 1 | 2 | 3 | 1 | 2 | 3 |
| Inlet temperature | (° C.) | 201 | 201 | 201 | 201 | 201 | 201 | 201 | 201 | 201 | 201 | 201 | 201 |
| Outlet temperature | (° C.) | 225 | 225 | 225 | 226 | 226 | 226 | 228 | 228 | 228 | 230 | 230 | 230 |
| Hot spot temperature | (° C.) | 253 | 253 | 253 | 256 | 256 | 256 | 260 | 260 | 260 | 251 | 251 | 251 |
| Coolant temperature | (° C.) | 220 | 220 | 220 | 220 | 220 | 220 | 220 | 220 | 220 | 220 | 220 | 220 |
| Inlet pressure | (barg) | 6.00 | 6.00 | 6.00 | 6.00 | 6.00 | 6.00 | 6.00 | 6.00 | 6.00 | 6.00 | 6.00 | 6.00 |
| Excess of oxygen vs. HCl* | (over stoich.) | 0.8 | 3.0 | 6.8 | 2.0 | 4.3 | 6.6 | 2.9 | 4.4 | 6.1 | 1.5 | 3.5 | 6.5 |
| Pressure drop | (bar) | 1.6 | 1.6 | 1.6 | 1.9 | 1.9 | 1.9 | 2.10 | 2.10 | 2.10 | 1.85 | 1.85 | 1.85 |
| HCl conversion | (% mol) | 98.4 | 99.9 | 100 | 98.5 | 99.8 | 100 | 98.4 | 99.1 | 99.6 | 97.9 | 98.4 | 99.5 |
| Selectivity to EDC | (% mol) | 98.28 | 98.63 | 98.68 | 98.19 | 98.40 | 98.55 | 97.96 | 98.23 | 98.36 | 98.25 | 98.55 | 98.63 |
| Ethyl chloride | (% mol) | 0.80 | 0.60 | 0.50 | 0.80 | 0.60 | 0.55 | 0.74 | 0.65 | 0.55 | 0.85 | 0.65 | 0.56 |
| Chlorinated by-products | (% mol) | 0.60 | 0.40 | 0.40 | 0.70 | 0.65 | 0.50 | 1.00 | 0.80 | 0.70 | 0.50 | 0.35 | 0.32 |
| COx | (% mol) | 0.32 | 0.37 | 0.42 | 0.31 | 0.35 | 0.40 | 0.30 | 0.32 | 0.39 | 0.40 | 0.45 | 0.49 |

*=[1−(4*O2/HCl)]*100

The reactor loading pattern used, the same for the different types of catalysts tested, was formed of five layers. From the top to the bottom the layers were as follows: 1)1200 mm long, containing a catalyst with 9.5 wt % of $CuCl_2$ and 5.7 wt % of KCl diluted to 30 vol % with graphite (cylinders with diameter of 5 mm and length of 6.2 mm); 2) 1200 mm long, containing a catalyst with 9.5 wt % of $CuCl_2$ and 5.7 wt % of KCl diluted to 40 vol %; 3) 1200 mm long, containing a catalyst with 9.5 wt % of $CuCl_2$ and 5.7 wt % of KCl diluted to 60 vol %; 4) 1000 mm long, containing a catalyst with 17.0 wt % of $CuCl_2$ and 1.5 wt % of KCl diluted to 45 vol %; 5) 2400 mm long, containing a catalyst with 17.0 wt % of $CuCl_2$ and 1.5 wt % of KCl not diluted. The overall catalytic bed was 7 m long.

A large number of tests were carried out and the main results are reported in Table 3. It is evident that the catalyst of the present invention (A) is superior in performance, giving the better combination in terms of selectivity, HCl conversion, pressure drop and hot spot temperatures compared to the other catalysts. The lower HCl conversion of the D catalyst is related to the very low amount of the catalyst in the reactor as a consequence of the too high catalytic bed void; also trying to increase the active phase and additive weight percentages in the catalyst to balance the lower amount of catalyst, the experimental HCl conversion obtained is again lower, because of the low surface area (below 90 $m^2$/g) obtained. Moreover the measured pressure drop of the D catalyst is higher than expected on the basis of the catalyst characterizations, because of the unavoidable breakage during the loading of this catalyst formed via extrusion.

It is believed that the reasons for the superior performance of the catalysts of the invention are as follows.
(i) In comparison with catalyst B, i.e. the catalyst of U.S. Pat. No. 4,366,093, the present catalysts are somewhat longer, (6.1–6–9 mm against 3–6 mm), allowing an increase of the bed void in the reactors. As a consequence a reduced pressure drop of the catalytic bed, a better heat exchange (therefore lower hot spot temperatures), an increased catalyst life and reduced by-products formation are achieved, as shown in the above Table 3. The lower amount of active phase per volume of reactor can be balanced with an increase of the active phase at values not influencing significantly the value of surface area of the final catalyst.
(ii) U.S. Pat. No. 4,740,644 (exemplified above by catalyst C) reports the use of a catalyst in pellets with similar external diameter (5 mm), and shorter length (5 mm instead of 6.1–6–9 mm). The greater length of the new catalyst allows a higher bed void and the consequent improvement in terms of lower pressure drop and better heat exchange, as shown in Table 3.

(iii) In the case of the catalysts of U.S. Pat. No. 5,166,120, (catalyst D above) the pellets are longer than those of the present invention, the examples considering pellets with a length of 11±2 mm. Pellets so long and with variable length, because of their preparation method (extrusion), give loading problems in industrial oxychlorination tubes, with consequently no homogeneous and reproducible pressure drop and catalyst amount among the tubes of the reactor. Furthermore this larger pellet length implies a large reduction in the active phase content per volume of reactor (compared to the catalyst of the present invention), which cannot be easily balanced only by increasing the active phase content of the pellets.

What is claimed is:

1. A process for the catalytic oxychlorination of hydrocarbons comprising reacting said hydrocarbons, oxygen and hydrogen chloride in the presence of a catalyst comprising a carrier and catalytically active material, said catalytically active material comprising copper and being supported on said carrier, said copper being present in an amount of 1% to 12% by weight of said catalyst, wherein said catalyst is in the form of a hollow cylinder having external diameter represented by $D_e$, internal diameter represented by $D_i$ and length represented by L, wherein $D_e$ is from about 4 mm to about 7 mm, $D_i$ is from about 2 mm to about 2.8 mm, L is from about 6.1 mm to about 6.9 mm, and the ratio $D_e/D_i$ is from about 2 to about 2.5.

2. The process of claim 1 wherein $D_e$ is from about 4.5 mm to about 5.5 mm, $D_i$ is from about 2 mm to about 2.6 mm, L is from about 6.2 mm to about 6.6 mm, and the ratio $D_e/D_i$ is from about 2.1 to about 2.3.

3. The process of claim 1 wherein said catalytically active material further comprises at least one metal, said metal being an alkali metal, an alkaline earth metal, a group IIIB metal, or a lanthanide, said metal being present in an amount up to 10% by weight of said catalyst.

4. The process of claim 2 wherein said catalytically active material further comprises at least one metal, said metal being an alkali metal, an alkaline earth metal, a group IIIB metal, or a lanthanide, said metal being present in an amount up to 10% by weight of said catalyst.

5. The process of claim 3 wherein said alkali metal is lithium or potassium, said alkaline earth metal is magnesium, and said lanthanide is lanthanum or cerium, wherein said metal is present in an amount up to 6% by weight of said catalyst.

6. The process of claim 4 wherein said alkali metal is lithium or potassium, said alkaline earth metal is magnesium, and said lanthanide is lanthanum or cerium, wherein said metal is present in an amount up to 6% by weight of said catalyst.

7. The process of claim 1 wherein said carrier is silica, pumice, diatomaceous earth, alumina, boehmite or bayerite.

8. The process of claim 2 wherein said carrier is silica, pumice, diatomaceous earth, alumina, boehmite or bayerite.

9. The process of claim 3 wherein said carrier is silica, pumice, diatomaceous earth, alumina, boehmite or bayerite.

10. The process of claim 4 wherein said carrier is silica, pumice, diatomaceous earth, alumina, boehmite or bayerite.

11. The process of claim 7 wherein said carrier is alumina having a surface area ranging from about 50 $m^2/g$ to about 350 $m^2/g$.

12. The process of claim 8 wherein said carrier is alumina having a surface area ranging from about 50 $m^2/g$ to about 350 $m^2/g$.

13. The process of claim 9 wherein said carrier is alumina having a surface area ranging from about 50 $m^2/g$ to about 350 $m^2/g$.

14. The process of claim 10 wherein said carrier is alumina having a surface area ranging from about 50 $m^2/g$ to about 350 $m^2/g$.

15. The process of claim 1 wherein said catalyst or said carrier is formed on a tableting machine.

16. The process of claim 2 wherein said catalyst or said carrier is formed on a tableting machine.

17. The process of claim 3 wherein said catalyst or said carrier is formed on a tableting machine.

18. The process of claim 4 wherein said catalyst or said carrier is formed on a tableting machine.

19. The process of claim 13 wherein said carrier is formed on a tableting machine and thereafter impregnated with said catalytically active material.

20. The process of claim 14 wherein said carrier is formed on a tableting machine and thereafter impregnated with said catalytically active material.

21. The process of claim 15 wherein said carrier is formed on a tableting machine and thereafter impregnated with said catalytically active material.

22. The process of claim 16 wherein said carrier is formed on a tableting machine and thereafter impregnated with said catalytically active material.

23. A process for the catalytic oxychlorination of ethylene to 1,2-dichloroethane comprising reacting said ethylene, oxygen and hydrogen chloride in a fixed bed reactor in the presence of a catalyst comprising a carrier and catalytically active material, said catalytically active material comprising copper and being supported on said carrier, said copper being present in an amount of 1% to 12% by weight of said catalyst, wherein said catalyst is in the form of a hollow cylinder having external diameter represented by $D_e$, internal diameter represented by $D_i$ and length represented by L, wherein $D_e$ is from about 4 mm to about 7 mm, $D_i$ is from about 2 mm to about 2.8 mm, L is from about 6.1 mm to about 6.9 mm, and the ratio $D_e/D_i$ is from about 2 to about 2.5.

24. The process of claim 23 wherein $D_e$ is from about 4.5 mm to about 5.5 mm, $D_i$ is from about 2 mm to about 2.6 mm, L is from about 6.2 mm to about 6.6 mm, and the ratio $D_e/D_i$ is from about 2.1 to about 2.3.

25. The process of claim 23 wherein said catalytically active material further comprises at least one metal, said metal being an alkali metal, an alkaline earth metal, a group IIIB metal, or a lanthanide, said metal being present in an amount up to 10% by weight of said catalyst.

26. The process of claim 24 wherein said catalytically active material further comprises at least one metal, said metal being an alkali metal, an alkaline earth metal, a group IIIB metal, or a lanthanide, said metal being present in an amount up to 10% by weight of said catalyst.

27. The process of claim 25 wherein said alkali metal is lithium or potassium, said alkaline earth metal is magnesium, and said lanthanide is lanthanum or cerium, wherein said metal is present in an amount up to 6% by weight of said catalyst.

28. The process of claim 26 wherein said alkali metal is lithium or potassium, said alkaline earth metal is magnesium, and said lanthanide is lanthanum or cerium, wherein said metal is present in an amount up to 6% by weight of said catalyst.

29. The process of claim 23 wherein said carrier is silica, pumice, diatomaceous earth, alumina, boehmite or bayerite.

30. The process of claim 24 wherein said carrier is silica, pumice, diatomaceous earth, alumina, boehmite or bayerite.

31. The process of claim 25 wherein said carrier is silica, pumice, diatomaceous earth, alumina, boehmite or bayerite.

32. The process of claim 26 wherein said carrier is silica, pumice, diatomaceous earth, alumina, boehmite or bayerite.

33. The process of claim 29 wherein said carrier is alumina having a surface area ranging from about 50 $m^2/g$ to about 350 $m^2/g$.

34. The process of claim 30 wherein said carrier is alumina having a surface area ranging from about 50 $m^2/g$ to about 350 $m^2/g$.

35. The process of claim 31 wherein said carrier is alumina having a surface area ranging from about 50 $m^2/g$ to about 350 $m^2/g$.

36. The process of claim 32 wherein said carrier is alumina having a surface area ranging from about 50 $m^2/g$ to about 350 $m^2/g$.

37. The process of claim 23 wherein said catalyst or said carrier is formed on a tableting machine.

38. The process of claim 24 wherein said catalyst or said carrier is formed on a tableting machine.

39. The process of claim 25 wherein said catalyst or said carrier is formed on a tableting machine.

40. The process of claim 26 wherein said catalyst or said carrier is formed on a tableting machine.

41. The process of claim 35 wherein said carrier is formed on a tableting machine and thereafter impregnated with said catalytically active material.

42. The process of claim 36 wherein said carrier is formed on a tableting machine and thereafter impregnated with said catalytically active material.

43. The process of claim 37 wherein said carrier is formed on a tableting machine and thereafter impregnated with said catalytically active material.

44. The process of claim 38 wherein said carrier is formed on a tableting machine and thereafter impregnated with said catalytically active material.

* * * * *